United States Patent [19]
Adams

[11] 3,945,387
[45] Mar. 23, 1976

[54] IMPLANTABLE CARDIAC PACER WITH CHARACTERISTIC CONTROLLABLE CIRCUIT AND CONTROL DEVICE THEREFOR

[75] Inventor: Theodore P. Adams, Wauwatosa, Wis.

[73] Assignee: General Electric Company, Schenectady, N.Y.

[22] Filed: Sept. 9, 1974

[21] Appl. No.: 504,346

[52] U.S. Cl. ...... 128/419 PG; 307/223 R; 335/206; 335/306
[51] Int. Cl.² .................................. A61N 1/36
[58] Field of Search ...... 128/419 E, 419 P, 419 PG, 128/419 PT, 421, 2 R, 2.1 A; 307/223 C, 223 R; 335/206, 207, 306

[56] References Cited
UNITED STATES PATENTS

| | | | |
|---|---|---|---|
| 3,311,111 | 3/1967 | Bowers | 128/419 PG |
| 3,623,486 | 11/1971 | Berkovits | 128/419 PG |
| 3,631,860 | 1/1972 | Lopin | 128/419 PG |
| 3,639,740 | 2/1972 | Escoffier et al. | 307/223 R |
| 3,646,940 | 3/1972 | Timm et al. | 128/427 |
| 3,672,352 | 6/1972 | Summers | 128/2.1 A |
| 3,805,796 | 4/1974 | Terry, Jr. et al. | 128/419 PG |
| 3,830,621 | 8/1974 | Miller | 335/306 |
| 3,864,173 | 2/1975 | Butschkau | 335/206 |

Primary Examiner—William E. Kamm
Attorney, Agent, or Firm—Ralph G. Hohenfeldt; Fred Wiviott

[57] ABSTRACT

An implantable cardiac pacer has a counter for encoding different binary numbers in response to clock pulses applied thereto through an internal clock pulse generating switch that can be activated from outside of the subject's body by application of radiant energy. The binary numbers are decoded with switches that sequentially connect and disconnect circuit elements to control a characteristic of the pacer such as its stimulus pulse width, pulse amplitude, pulse rate and others. The clock pulse switch may be one that is activated with light or pressure but is preferably a magnetic switch system controlled by a shaped magnetic field for preventing inadvertent operation. The encoder counter recycles or resets to its initial value when a predetermined number of clock pulses are applied.

11 Claims, 7 Drawing Figures

IMPLANTABLE CARDIAC PACER WITH CHARACTERISTIC CONTROLLABLE CIRCUIT AND CONTROL DEVICE THEREFOR

BACKGROUND OF THE INVENTION

This invention concerns means for adjusting or selecting various operating characteristics of an implantable cardiac pacer without physically contacting the pacer.

Implantable cardiac pacers are essentially resin encapsulated pulse generators which can be connected to the heart to apply stimulus pulses thereto. In some subjects asynchronous pulse generators are used. This type of pulse generator applies stimulus pulses at a constant rate and each pulse has a substantially constant width and amplitude. Asynchronous pacers are usually used in subjects who have complete ventricular conductive block wherein no natural electric stimuli are produced by the heart.

The standby pacer is another type that is commonly used. In this type, there is a pulse generator and a sensing circuit connected to the heart. When a natural electric stimulus occurs on the heart, the sensing circuit causes the pulse generator to be inhibited for a time interval. The sensing circuit may be made to exhibit hysteresis. That is, when a natural stimulus is sensed, the next pulse to be generated by the generator may be delayed for a relatively long interval and if a natural pulse does not occur within that interval the generator will turn on and pulse at shorter intervals or at a higher rate until the next natural pulse, if any occurs. Sensing circuits also usually have a refractory period during which they will not respond to noise or other electric signals on the heart following the moment after a natural signal is sensed.

It is desirable that the foregoing functional parameters of the pacer be as compatible as possible with the physiological needs of each cardiac patient in which a pacer is implanted. Stated in another way, it is desirable to optimize the stimulus pulse rate, amplitude and width for each patient to meet physiological needs and also to conserve battery energy and in many cases it would be desirable to be able to select the refractory interval, the hysteresis interval and sensitivity of the sensing circuit after the pacer has been surgically implanted.

SUMMARY OF THE INVENTION

An object of this invention is to provide an electric organ stimulator, such as a cardiac pacer with means for adjusting any desired operation characteristic thereof over a wide range without entering the pacer itself nor invading the body of the subject in which the pacer is implanted.

Another object of this invention is to provide a pacer characteristic adjustment and selection means which occupies a minimum amount of space in the pacer and has a minimum number of components compared to prior art means for accomplishing the same purposes.

Another object is to provide a system and a device for remote adjustment and selection of pacer characteristics which is substantially immune from interference and inadvertent operation. Another object is to provide an implantable cardiac pacer with a circuit including switches that are magnetically operable and must be in predetermined states to alter a functional characteristic of the pacer and which will not attain said predetermined states when all switches are exposed to a stray magnetic field and to also provide a cooperating portable control device having magnets arranged with a field free region between them such that when the device is in a substantially singular position proximate to the pacer it will magnetically operate said switches to said predetermined states.

Another object is to provide for control of pacer characteristics by applying an external shaped magnetic field which is distinct from stray fields which may be encountered accidentally.

A further object is to provide operating characteristic control means in which there are substantially no moving parts and which is reliable and predictable in its operation.

Yet another object of this invention is to provide in a pacer an encoder that reponds to externally applied signals by producing coded binary numbers that are decoded to activate circuit elements in the pacer which bring about a change in an operating characteristic thereof.

Another important object of the invention is to provide recycling encoding means which allow stepping the operating characteristic to a predetermined value after which an additional external control signal will reset the decoder and hence the operating characteristic to its initial value.

How the foregoing and other more specific objects of the invention are achieved will appear in the detailed description of illustrative embodiments of the invention which will be set forth shortly hereinafter.

In general terms, the organ stimulus pulse generator with which the present invention is used may be an asynchronous or a synchronous type. The invention is exemplified in an asynchronous pacer. Various operating characteristics may be controlled in accordance with the invention, as will be evident later in the specification. Control of pulse rate is typical. This involves use of an encoding circuit such as a ring counter or shift register which produces a different binary number for each clock pulse that it receives. The clock pulses are controlled by a switch in the pacer and this may be a magnetically operated switch such as a reed switch controlled by a shaped or predetermined applied magnetic field or it may be an electric switch operated externally of the body with another form of radiation such as light or radio frequency radiation or it may be operated by pressure applied to the surface of the body in proximity with the pacer.

The encoded information is decoded such as to produce signals for operating switching devices that connect various circuit elements into characteristic controlling circuits of the pacer on a selective basis.

A more detailed description of a preferred embodiment of the invention will now be set forth in reference to the drawings.

DESCRIPTION OF A PREFERRED EMBODIMENT

Figure 1:
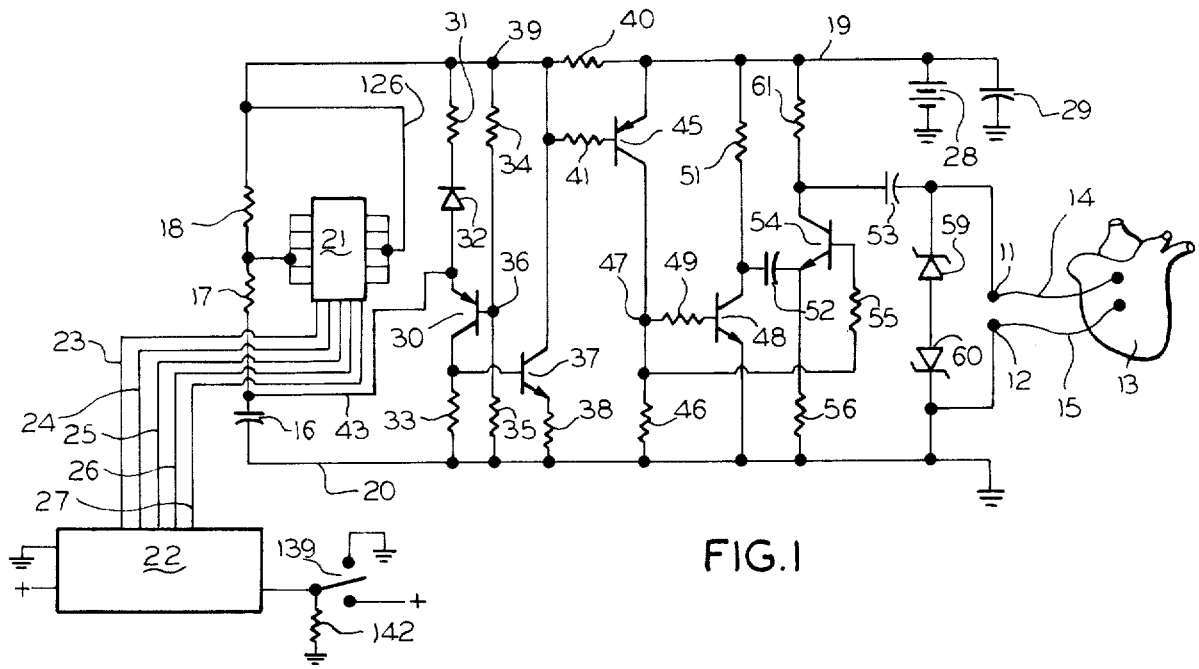
FIG. 1 is a circuit diagram of a cardiac pacer embodying the invention.

FIG. 1 is a diagram of a standby implantable cardiac pacer which incorporates the new operating characteristic selection device. The pacer comprises a pulse generator whose output terminals are toward the right portion of the drawing and are marked 11 and 12. These terminals are adapted to be connected in a circuit with the heart 13 by means of leads 14 and 15.

The rate at which artificial stimulus pulses are applied to the heart is governed by an RC timing circuit which is at the left and comprises a timing capacitor 16 in series with resistors 17 and 18. This series circuit is connected across d-c power source lines 19 and 20. The d-c source for energizing these lines is marked 28 and it has a filter capacitor 29 in parallel with it.

In accordance with the invention, a decoding device 21 for placing more or less resistance in parallel with timing resistor 18 to alter the pulse rate characteristic of the generator is shown in block form in FIG. 1 and will be described in detail later. Decoder 21 is connected to an encoder 22 by means of five control lines 23–27. Encoder 22 will also be described in detail later.

Basically, in FIG. 1 a stimulus pulse appears on output terminals 11 and 12 of the pacer when timing capacitor 16 at the left of the diagram reaches its trigger voltage level. A line 43 connects timing capacitor 16 to the first stage of pulse generator 10. The first stage of the pulse generator 10 includes a transistor 30 having its emitter and collector connected in series with a resistor 31, a diode 32 and a collector resistor 33. A voltage divider comprising resistors 34 and 35 provides bias to transistor 30 by virtue of the transistor base being connected to an intermediate point 36 in the bias circuit. When the voltage on capacitor 16 exceeds the sum of the voltages at point 36 and the emitter to base drop of transistor 30, transistor 30 conducts and begins to discharge capacitor 16 for initiating the rise portion of a timing pulse. The timing cycle is repeated usually about 72 times per minute in cardiac stimulators.

One of the discharge paths of capacitor 16 is through the load terminals, namely the emitter and collector of transistor 30 and resistor 33. The voltage developed on resistor 33 is applied to the control terminal or base of a transistor 37 which goes into saturation quickly. Transistor 37 has a comparatively small resistor 38 in its emitter circuit as one means for limiting capacitor discharge current. Resistor 38 also affects pulse width.

The charging time of capacitor 16 determines the pulse repetition rate characteristics and its discharge time determines pulse width characteristic. Pulse width control is obtained with the Schottky diode 32 in series with a pulse width determining resistor 31. The top of resistor 31 connects with source line 19 and to a junction point 39 which is separated from the d-c source terminals by a relatively high resistor 40. When capacitor 16 is charging, the junction point 39 of resistors 18, 31, 34 and 41 are all near battery potential, that is, junction point 39 is near battery potential. However, during the discharge cycle of capacitor 16, junction 39 changes to near ground or negative potential due to the high conductivity of saturated transistor 37. This results in all current from capacitor 16 and any current through resistor 40 from the battery flowing to ground during discharge of capacitor 16, thereby decoupling the battery from the timing circuit and eliminating any effect it might otherwise have on pulse width.

During the discharge cycle of capacitor 16, some of its current is diverted from transistor 30 through diode 32 and resistor 31 to common point 39. This diversion of current causes transistor 30 to turn off sooner than it would if the capacitor could discharge only through transistors 30 and 37 and it reduces the timing pulse width to about 1 millisecond or less if the proper values of resistors 31 and 38 are used.

Capacitor 16 actually discharges through several separate paths, one of which includes charging resistors 17 and 18. When the capacitor 16 discharges to a voltage level which is not sufficient for forward biasing transistor 30, the latter turns off and another charging cycle for capacitor 16 begins.

Each time timing capacitor 16 discharges, a negative going pulse of predetermined width is developed on the collector of transistor 37. This pulse is applied to the base of a transistor 45 through resistor 41, causing transistor 45 to become forward biased and conductive. Transistor 45 has a collector resistor 46 so that when the transistor conducts, a point 47 on the collector develops a positive pulse which is transmitted to a transistor 48 through a base resistor 49.

Transistor 48 has its emitter connected to ground or negative source terminal 20 and its collector connected to a collector resistor 51 which is in turn connected to positive supply line 19. When a positive pulse is applied to the base of transistor 48 concurrently with discharge of timing capacitor 16, a negative going pulse appears on this collector. The negative going pulse is coupled to the output circuit by means of capacitor 52.

In the load circuit there is a capacitor 53 which is charged simultaneously with timing capacitor 16. The charging circuit for capacitor 52 begins at positive line 19 and continues through resistor 51, capacitor 52 and a resistor 56 which is connected to negative line 20. The charging time of capacitor 52 is long compared to its own discharge time but is short compared to the charging time of capacitor 16. The other load circuit capacitor 53 is also charged at the same time as capacitor 52. The charging circuit for capacitor 53 begins at positive line 19 and includes a capacitor 53, the heart 13, and back to negative line 20 through heart tissue intervening between output terminals 11 and 12.

Capacitor 53 is also charged rapidly in comparison with timing capacitor 16 but is charged slowly in comparison with its discharge time. Because of the slow charging rate of capacitor 53, current flowing through the heart 13 is insufficient to stimulate it. On the other hand, rapid discharge of capacitor 53 does produce a high enough current to stimulate the heart. The low charging current through capacitor 53 and its high discharge current flow in equal and opposite directions through the heart. When capacitor 53 becomes fully charged, the output circuit remains inactive until initiation of a pulse by the timing circuit.

When a timing pulse is initiated, transistors 37, 45, 48 and 54 go into saturation. It will appear that transistors 48 and 54 are involved in rapid discharge of capacitor 53 to effect a stimulating pulse.

Transistor 45 has a bias resistor 41 connected between its base and the collector of transistor 37. When transistor 37 conducts, transistor 45 is forward biased from positive line 19 through the emitter of transistor 45, resistor 41, transistor 37 and its emitter resistor 38. Transistor 45 upon the appearance of a negative going pulse on its base begins to conduct and quickly goes into saturation. This causes a voltage to be developed across resistor 46 which is the collector resistor of transistor 45. This voltage is applied through resistor 49 to the base of transistor 48, forward biasing the latter into conduction. The voltage developed on resistor 46 by virtue of conduction of transistor 45 is also applied to transistor 54 through a biasing resistor 55. This causes transistor 54 to conduct. Conduction of transistors 48 and 54 allows a discharge path for capacitors 52 and 53. Starting with the left or positive plate of capacitor 53, this series discharge path includes transistor 54, capacitor 52, transistor 48, part of negative line 20, the heart 13 and finally to the right or negative plate of capacitor 53. Due to the very low discharge impedance in this circuit, a high energy stimulus pulse is conducted through the heart which is limited primarily by the relatively low impedance of the heart itself. The heart impedance is such that capacitors 52 and 53 do not discharge completely before timing circuit transistor 37 goes off after which transistors 45, 48 and 54 turn off quickly.

The output circuit is connected for doubling the source voltage in this example. At the initiation of a timing pulse, the emitter of transistor 54 is driven through a potential which is below ground by an amount approximately equal to the battery voltage 28 due to the rapid discharge of capacitor 52. When transistor 54 saturates an instant later, the positive or left plate of capacitor 53 is switched essentially from battery voltage B+ to −B+, a change which produces a potential of about −2B+ which is double the battery voltage across the heart load with one side of the heart reference to battery ground.

The output terminals 11 and 12 have a pair of reversely connected zener diodes 59 and 60 connected across them primarily to protect the pulse generator against the input of relatively high voltages such as might be developed in the body if a defibrillator is applied.

In accordance with the invention, the energy of the stimulus pulses may be varied or selected after the pacer is implanted. Basically, the stimulus pulse energy is governed by the value of resistor 61 which determines the charge level of heart coupling capacitor 53. The effective value of resistor 61 and, hence, the output pulse energy, may be modified after the pacer is implanted. For this purpose a decoder unit may be connected in parallel with resistor 61. This decoder unit may be basically similar to unit 21 in that it has several resistors and switches which may be coded to connect selectively in parallel with resistor 61 upon occurrence of a command pulse administered from outside of the subject's body. The associated encoder, not shown, in FIG. 1, may be similar to encoder 22 which is illustrated and will be described in detail hereinafter.

The means for selecting and controlling one or more of the operating characteristics of the cardiac pacer such as pulse rate, pulse width, output pulse amplitude and other characteristics too will now be described in detail. Consider, for example, the encoder 22 in FIG. 1 and its control lines 23–27 together with decoder 21 for controlling stimulus pulse rate. In FIG. 1 the decoder has a common line 125 connected to one side of timing resistor 18 and another common line 126 connected to the other end of timing resistor 18. Similar reference numerals are given to these lines in FIG. 2 where the decoder is generally designated by the numeral 21. The control lines 24–27 are also marked correspondingly and the encoder is again marked 22 generally. A pacer characteristic may be selected by operating a clock switch 139 which is symbolized as an electromechanical switch but may take many forms as will be evident later. Switch 139 is in the pacer and is not directly accessible from outside the body. A suitable switch is one that is operated from outside of the body by applying magnetic or electromagnetic energy or by applying physical pressure on the body. Switch 139 is shown as being supplied from a positive potential source, B+. Each time switch 139 is closed, a clock pulse is delivered to the encoder 22 to change its binary output number state and this number is decoded to effectuate change of an operating characteristic. A resistor 142 is connected between the clock line output and ground to prevent the clock line from floating potentially.

Encoder 22 may be variously embodied and may, for example, take the form of a ring counter or a shift register. In this example, a ring counter is used which comprises several master-slave type D flip-flops 130, 131, 132, 133 and 134. The dashed lines 135–137 suggest that additional flip-flops may be interposed between flip-flops 132 and 133. J-K master-slave flip-flops could also be used or the encoder may, for example, be a CD 4015A static shift register, not shown, with a self-resetting loop. Ring counter is used herein as the generic designation for ring counters and shift registers. Binary numbers may be encoded with the flip-flops through a range from 00000 to 10000 in the present example, the most significant bit appearing on output or control line 23 and the least significant bit appearing on control line 27.

The D-type flip-flops used here are characterized by transferring the state which exists on its D input to its Q output whenever a clock pulse is applied to its C input. In this case all of the C inputs are connected to a common bus 138 for simultaneously receiving a clock pulse through switch 139 that may be connected to the same positive voltage source which supplies the pacer pulse generator and sensing circuit described above. This switch may take a variety of forms, in accordance with the invention, as will be described later, but for present purposes switch 139 may be considered a magnetic reed switch that is embedded in the implanted pacer. Switch 139 may be closed by placing a permanent magnet, not shown, in FIG. 2, in proximity with the pacer. The magnet may be placed on the skin over the pacer and then withdrawn to close and open switch 139 and provide one clock pulse.

The ring counter comprised of the D flip-flops is somewhat conventional except that in this case, after it has been actuated through a complete sequence, it resets all outputs 23–27 at the zero state after which a new sequence of binary numbers may be produced on control lines 23–27 by pulsing switch 139 respectively.

The arrangement includes a NAND gate 140 which has several input each of which is connected to a corresponding Q̄ output of the respective flip-flops 130–133 but not to flip-flop 134. Assume for simplicity of explanation that at the time the pacer is assembled the flip-flops are sequenced such that all of the Q̄ outputs of flip-flops 130–133 are in their "1" or high state and all of the Q outputs are zero or low and that the Q output 23 of flip-flop 134 is high so the binary number 10000 will appear on control lines 23–27. Assuming that positive logic is used, when all the $\overline{Q}$ inputs to NAND gate 140 are high initially, the output of this gate is low. The NAND gate output is low only when all of its inputs are high. If any input is low the output will be high. Since the gate 140 output is low initially, the D input of the first flip-flop 130 will be high due to inversion by inverter 141. The Q output of flip-flop 130 will be low as will all the other Q outputs except that of flip-flop 134 initially. When the first clock pulse or high signal is applied by closing clock pulse switch 139 momentarily, the high signal on the input of flip-flop 130 will be transferred to its Q output and to control line 27 thus producing the binary number 00001 on the control lines with the least significant bit appearing on line 23. When the Q output of flip-flop 130 goes high, its $\overline{Q}$ output goes low such as to make the output of NAND gate 140 high and, because of inverter 141, a low or 0 now appears on the D input of flip-flop 130. When the next clock pulse is applied via switch 139, the low which existed on the D input of flip-flop 130 is transferred to its Q output but the previously existing high output of the flip-flop 130 is transferred to the Q output of flip-flop 131 so as to produce the binary number 00010. This sequence of zeroing the Q outputs and corresponding control lines of the flip-flops is continued until the next to the last flip-flop 133 has 1 or high appearing on its Q output and control line 24. The encoded number is then 01000. When this stage in the sequence is reached, the $\overline{Q}$ outputs of the four flip-flops 130–133 will be high and the Q outputs of these flip-flops will be low. The next clock pulse from switch 139 will transfer the high on the D input of flip-flop 134 to its Q output producing the binary number 10000 in the control lines. Since prior to the last step all of the $\overline{Q}$ outputs of flip-flops 130–133 have gone low, all inputs to NAND gate 140 will be high and its output will go low so that, due to inverter 141, the D input to the first flip-flop will go high which is the initial state again. When the next clock pulse is applied through switch 139, the high existing on the D input of flip-flop 130 will be transferred to its Q output so that a 1 will appear on control line 27 and the binary number 00001 will be produced again. The Q output of flip-flop 134 will then be zero. Thus, it will be seen that the ring counter continues to recycle as clock pulses are applied consecutively through switch 139.

In this example, control lines 23–27 run to the gates of several field effect transistors 145–149 used as switches and comprising the decoder 21. Other types of controllable switches could be substituted. The transistors are rendered conductive in this case in the order of 145 to 149 by the binary numbers 00001 to 10000 consecutively produced by encoder 22. Thus, the transistors serve as switches for connecting the resistors consecutively across terminals 126 and 127 which, in this particular example, are connected in parallel with timing resistor 18 by way of terminals 126 and 127. The resistors preferably each have different values so that when they are in parallel with resistor 18, a unique charging time for timing capacitor 16 will exist. This means that the time interval or rate of the pulse generator can be varied as desired within the limits of the number and values of resistors 150–154 connected in parallel therewith.

Those skilled in the art will recognize that capacitors or other circuit elements could be substituted for resistors 150–154 where it is desired to change an operating characteristic by varying capacitance.

Individual encoders such as encoder 22 which has just been described may also be incorporated in the pacer to cooperate with various other decoders such as one paralleling resistor 31 for changing pulse width or one paralleling resistor 61 for changing pulse amplitude. In each case resistors or other circuit elements of proper value would be connected in series with the field effect transistor switches in the decoder 21. In any case, a separate encoder-decoder combination and control switch is needed for each pacer characteristic that is controlled.

Although the number of elements involved in the ring counter circuit and in encoding and decoding control signals seems formidable, it will be appreciated by those skilled in the art that all of these components including the field effect transistors and the flip-flops can be formed on an integrated circuit chip of under 100 mils square for each set of flip-flops, the inverter, the NAND gate and the transistor switches. Thus, the new pacer characteristic control system will generally occupy less space than a single reed switch even though as many as six characteristics are controlled. Usually, however, it will be sufficient to permit selection of the rate, width and amplitude of the stimulus pulses. When more than one characteristic is controlled from externally of the subject, switches responsive to different radiation media or other means for discriminating must be used.

Figure 2:
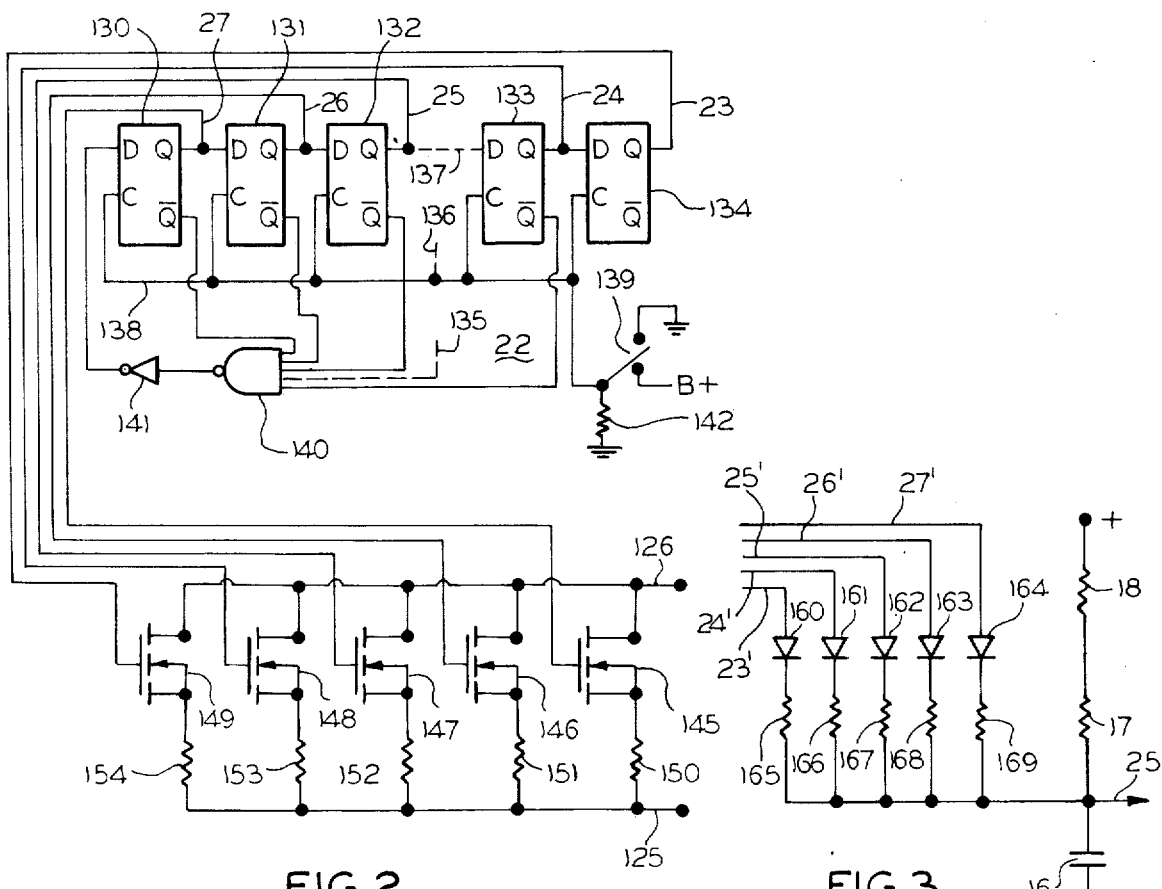
FIG. 2 is a block diagram of an encoding and decoding system used in the previous embodiment.
Figure 3:
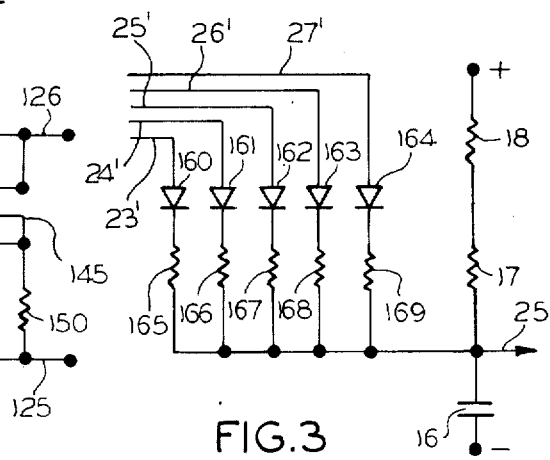
FIG. 3 is a modified version of the decoder system for use in the FIG. 1 circuit.
Figure 4:
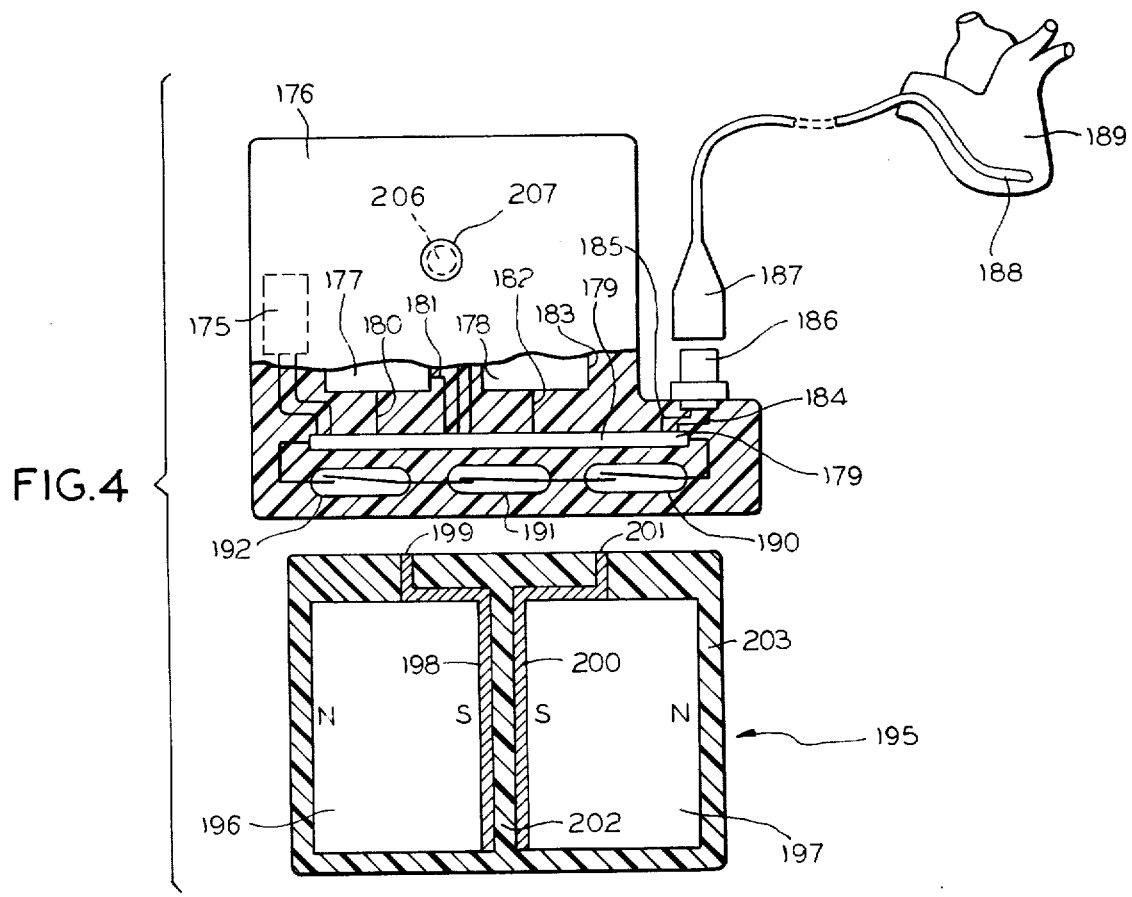
FIG. 4 represents an implantable cardiac pacer having portions broken away, a heart and a specialized control magnet.

FIG. 3 shows another type of decoder which may be used to control pulse rate in place of decoder 21 shown in FIG. 2. In FIG. 3 timing capacitor 16 and charging resistors 17 and 18 of the pulse generator are reproduced. In this case, however, instead of switching resistors in parallel with timing resistors 17 and 18, the timing capacitor 16 is merely connected to a voltage source through alternate charging paths comprised of diodes 160–164 in series with resistors 165–169, respectively. The anodes of the diodes are connected to the encoder control lines which are marked 23' to 27' in FIG. 3 and correspond with 23–27 in FIG. 2. The encoder 22, for example, may then supply a charging voltage to the diode through a resistor so as to charge timing capacitor 16 more rapidly than it would be charged if it were charged from positive line only through resistors 17 and 18. In other words, a charging voltage is derived from the encoder itself. Thus, if line 27' goes high, which would correspond with encoder 22 having an output state of 00001, diode 164 will be forward biased and it will pass current through resistor 169 to charge capacitor 16 at a supplementary rate dependent on the value of resistor 169 and the high state potential of the encoder output terminals. Each of the resistors 165–169 have different values to change the supplementary charging rate since the voltages applies sequentially to control line 23'–27' are assumed to be equal.

Where a single implanted magnetic reed switch 139 is used for stepping a shift register or a ring counter such as in encoder 22 by bringing a magnet external to the body in proximity with the switch, it will be evident that there is a possibility of the subject in which a pacer is implanted coming into proximity with a magnet that could operate the switch inadvertently. In accordance with another aspect of the invention, a magnetically operable switch such as 139 is precluded from inadvertent operation by stray magnetic fields by providing for operation only by externally applied magnetic fields which have a predetermined shape. FIG. 4 shows a pacer in which switch operation by stray magnetic fields is precluded by using more than one magnetic reed switch for the switching function. In FIG. 4 pacer is shown schematically. It comprises resin encapsulating material 176 in the top portion of which the electric sources such as batteries 177 and 178 for driving the pacer are located. The electronic circuitry such as the pulse generator and heart sensing circuit are symbolized by the box 179 to which leads 180–183 extend from the batteries 177 and 178. A pair of conductors 184 run from electronic circuitry 179 to a connector 186 which may be assumed to contain the output terminals 11 and 12 of the pulse generator. A two conductor catheter 187 is shown adjacent connector 186 and the active end 188 of the catheter is disposed in a heart 189. The logic for charging a characteristic of the pacer which has been described above is represented by the box 175.

The pacer in FIG. 4 is provided with three series connected magnetic reed switches 190, 191 and 192 which together supplant switch 139 for providing control pulses to the encoder. Switches 190 and 192 are normally open and switch 191 is normally closed in this example. The purpose of this arrangement, as indicated earlier, is to preclude application of a clock pulse to the encoder when the implanted pacer is exposed inadvertently to a steady state or a-c magnetic field which would close a normally open single reed switch if only one clock pulse switch such as 139 were used. However, in this case all three switches 190–192 must be closed and this can only be done by applying a shaped or predetermined magnetic field such as may be done with a magnet assembly that is generally designated by the reference numeral 195.

With multiple switches, if the subject is exposed inadvertently to a stray state or a-c magnetic field such that switch 190, for example, would close, switch 192 will remain open to prevent generation of a clock pulse. If the field were strong enough to close switch 192 simultaneously with switch 190, the field will also be coupled with and strong enough to open switch 191 in which case application of a control pulse will again be prevented.

Center reed switch 191 should preferably be more sensitive to magnetic fields than the other switches 190 and 192 so switch 191 will open first if the switches are exposed simultaneously to a uniform stray magnetic field. An intrinsically more sensitive reed switch 191 may be used or the other switches 190 and 192 may be made less sensitive to a magnetic field by cutting their leads shorter. This reduces their magnetic permeability because the leads are made of magnetic material.

The magnet assembly 195 in FIG. 4 is provided to enable intentional closure of switches 190, 191 and 192 simultaneously. This assembly comprises two permanent magnets 196 and 197 which are arranged closely adjacent each other with similar poles such as the south poles, in opposition as indicated by the letter S on the magnets. Contiguous with the south pole of magnet 196 is an iron pole piece 198 which terminates in a pole face 199. Similarly, contiguous to magnet 197 is a pole piece 200 which terminates in a face 201. The space between pole pieces 198 and 200 is occupied by resin 202 and the whole magnet assembly is encapsulated in resin which is generally marked 203. The magnetic field from magnet 196 extends from the pole face 199 to the north or N pole of this magnet. The magnetic field of magnet 197 extends from pole face 201 to the north pole of this magnet. There is substantially no magnetic field coupling pole faces 199 and 201 because of their similar polarities. Thus, the magnet assembly 195 produces two spaced apart diverging magnetic fields with an intervening region of no field between them. When the magnet assembly 195 is positioned as shown in FIG. 4 with respect to reed switches 190, 191 and 192, outside switches 190 and 192 will be coupled with magnetic fields and they will close and switch 191 will remain normally closed since it is in a region substantially void of a magnetic field. It is only when magnet assembly 195 is positioned substantially as it is shown in FIG. 4 that all three switches will close to provide a clock pulse to the encoder. If the magnet assembly is shifted to the right from its FIG. 4 position, it may close outside switch 190 but it will also open center switch 191 such that application of a clock pulse is prevented. Moreover, switch 192 will remain open under these circumstances. If the magnet is shifted to the left, switch 192 may close but switch 190 would remain open. It should be evident, therefore, that it is only when two magnetic fields are coupled with switches 190 and 192 while there is no coupling with switch 191 that a clock pulse will be produced.

As explained above, any uniform stray magnetic field which closes switches 190 and 192 will have previously opened more sensitive switch 191 to preclude a clock pulse. A stray field which closes switch 190, for example, would not result in a clock pulse because 192 would still be open and, if it were not, switch 191 would be opened. Thus, it is only when the magnet assembly is properly positioned or aligned that all three switches will be closed. This can be achieved by the subject sliding the magnet assembly 195 over the surface of the body where the pacer is implanted.

Figure 5:
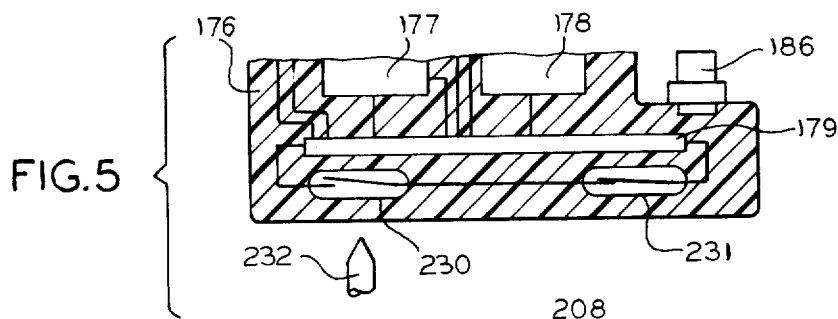
FIG. 5 is a reproduction of the fragmentary sectional portion of the pacer in FIG. 1 associated with a fragment of a control magnet for illustrating an alternative embodiment of the illustration.

An alternate switching system that is substantially immune to being operated unintentionally by a stray magnetic field but can be operated in a desired mode intentionally with a shaped or predetermined field configuration is shown in FIG. 5 where like parts are given the same reference numbers used in FIG. 4.

In FIG. 5, a normally open magnetic reed switch 230 and a normally closed reed switch 231 are embedded in the resin encapsulation 176 of the pacer. Closed switch 231 is preferably more sensitive so it will open with a magnetic field being applied that is weaker than the field required to close the other switch 230. Assume in this example that switch 230 must close while switch 231 remains closed to produce a control signal for changing a functional characteristic of the pacer. Hence, as the pacer enters a stray field the more sensitive normally closed switch will assuredly open before the other switch 230 closes, if it closes at all, to thereby prevent a characteristic control signal from being produced. Even if switches 230 and 231 are equally sensitive, a sufficiently strong stray field which couples with both of them and which would close switch 230 undesirably will open switch 231 and a considerable amount of protection against interferring fields is provided.

In accordance with the invention, however, selective closure of switch 230 can be obtained without opening switch 231 by using a pencil-like magnet 232 the tip of which is shown in FIG. 5. The pointed tip results in a concentrated or confined field being produced which field may be directed into switch 230 to close it without coupling with switch 231 such as to open it. If, when the physician is probing over the skin under which the pacer is implanted, the normally closed switch 231 is unintentionally opened, no harm will be done since it is only when switches 230 and 231 are both closed that an intentional switching function occurs.

It should also be noted that switch 230 will open before switch 231 closes when a stray magnetic field is removed. Thus, the switching circuit is always open in the presence of a strong magnetic field which is likely to be encountered accidentally. On the other hand, a field which is concentrated on the one switch 230 to close it, is unlikely to be encountered accidentally.

Those skilled in the art will appreciate that use of a predetermined magnetic field configuration to selectively control one or more switches is not limited to having three switches connected in series in a row as in FIG. 4 nor to having two in a row as in FIG. 5 for various combinations of opened and closed switches may be arranged and connected in various patterns with selected spacing between them.

Figures 6, 7:
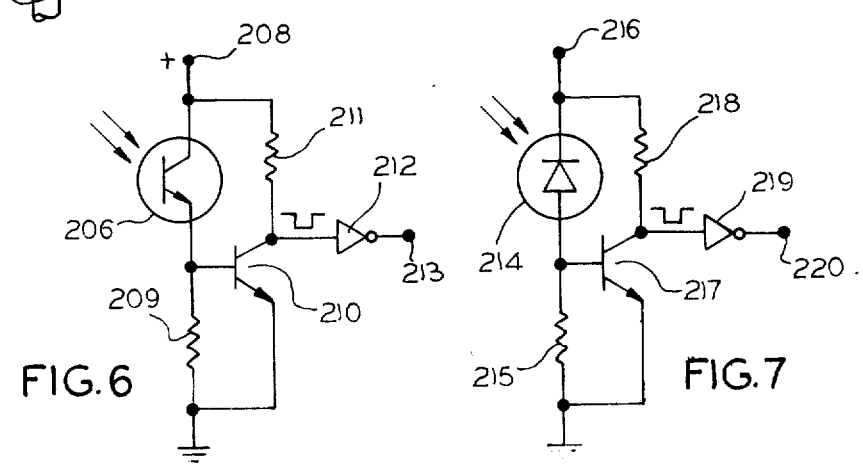
FIGS. 6 and 7 are phototransistor and photodiode switching circuits which may be substituted in the circuits of FIGS. 1 and 2.

An alternative to magnetic switches for applying clock pulses to the encoder is the switching circuit shown in FIG. 6. This is a light activated switching circuit which uses a phototransistor 206 that can be located under a lens 207 which is sealed into the pacer encapsulation as illustrated in FIG. 4. This switching circuit is operated to apply a clock pulse to the encoder by placing an intense light source on the surface of the body over the region in which the pacer is implanted.

It has been found that sufficient light will pass through body tissue as thick as one-half inch to activate the phototransistor. The body tissue is quite transmissive of the red part of the spectrum which, fortunately, is the part to which presently available phototransistors are most sensitive.

In FIG. 6 phototransistor 206 has a terminal 208 which may connect internally of the pacer to its power supply. When phototransistor 206 conducts due to application of light to the subject's body over the pacer, a voltage is developed across a resistor 209. The top of this resistor is connected to the base-emitter circuit of a transistor 210 which becomes conductive. The collector resistor of transistor 210 is marked 211. When transistor 210 conducts, a negative going pulse is produced on its collector. This pulse is coupled through an inverter 212 such that the output pulse on terminal 213 will be positive going. Terminal 213 may be connected where the terminal of switch 139 in FIGS. 1 and 2 is connected such as to introduce the positive pulse to encoder 22. Of course, if negative logic is used, inverter 212 would be unnecessary.

An alternative light activated switching circuit is shown in FIG. 7. This circuit uses a photodiode 214 in series with a resistor 215. This series circuit is connected to the pacer power source at its terminal 216. The base-emitter circuit of a transistor 217 is connected across resistor 215. The transistor has a collector resistor 218. When photodiode 214 is made conductive by exposure to light transmitted through the subject's tissue, the voltage drop across resistor 215 forward biases transistor 217 such as to make it conductive through its collector-emitter circuit. When it conducts, a negative pulse is produced on its collector and it may be inverted with an inverter 219 to produce a positive pulse on terminal 220 which may be introduced into the encoder for producing a unique binary number.

An alternative to using light activated switching devices as in FIGS. 6 and 7 is to use a pressure sensitive mechanical switch or a pressure sensitive semiconductive device, not shown. Those skilled in the art will appreciate that such devices may be used in conjunction with a suitable amplifier for producing a control signal in response to pressure. In a pacer, such devices may be disposed under a sealed diaphragm such as to be operated when a force is applied to the subject's body for transmission through a tissue to the subject's body for transmission through tissue to the pressure sensitive device.

The various encoders may also be operated with radio frequency receivers incorporated in the implanted unit. In such case each receiver may be tuned to a different frequency and produce an output signal when the frequency is received. An external transmitter, not shown, that is tunable to the various frequencies may be used selecting the characteristic of the pacer that is to be modified after implantation.

In cases where several different operating characteristics are to be subject to control in a single pacer, it is necessary for the decoders to be able to discriminate the various externally applied control signals lest one characteristic be modified when modification of another is intended. It should be evident from the description thus far that one way of accomplishing this is to use magnetic reed switches, a light activated device and a pressure sensitive device in combination for generating control signals. Of course, discrimination is obtainable when tuned radio frequency systems are employed. Another possibility is to use logic circuitry for discriminating.

In summary, an encoding and decoding system has been described for controlling the various operating characteristics of a pacer and several switching for introducing unique control signals from outside of the subject's body have been described as well. Although the invention has been described in considerable detail, such description is intended to be illustrative rather than limiting, for the invention may be variously embodied and is to be limited only by interpretation of the claims which follow.

I claim:
1. An implantable cardiac pacer comprising:
   a. pulse generator means for applying stimulus pulses to a heart, said generator means having at least one operating characteristic that is subject to variation,
   b. means for detecting control signals generated remotely from said pacer,
   c. ring counter means having a plurality of output terminals, said ring counter means being responsive to each in a succession of detected control signals by respectively changing the voltage states on said output terminals from a first state to different states to thereby produce a sequence of binary number representative signals on said output terminals,
   d. means connected with said output terminals and responsive to each binary number change thereon by varying said characteristic,
   e. means for resetting said ring counter means for its output terminals to attain said first state in response to a predetermined number of binary number states having occurred, f. said ring counter means comprising a series of interconnected flip-flops, said flip-flops respectively having output terminals (Q) and clock input signal terminals (C) and data input terminals, said flip-flops each being characterized by transferring whichever high or low state signal is on its data input terminal to its Q output terminal when a clock signal is applied to its C input terminal, g. said Q output terminal of the first and next flip-flops other than the last flip-flop in the series being connected to the ensuing data input terminal of subsequent flip-flops, h. said C input terminal being connected for simultaneously receiving a clock signal corresponding with each detected signal for sequentially advancing a signal that is initially on the data input terminal of the first flip-flop to the Q output terminal of the last flip-flop.

i. gate means having a plurality of input terminals connected to receive signals opposite of the signals on the Q output terminals, respectively, of each but the last flip-flop in said series, said gate means having an output terminal coupled with the data input terminal of said first flip-flop, the output terminal of said gate means changing state when the flip-flops other than the last flip-flop are operated to have their output terminals all at the same state to thereby apply an initializing signal state to the data input terminal of said first flip-flop and to establish the Q input terminal of the last flip-flop in a final state corresponding with said initial state, whereby the next detected control signal will start recycling of said flip-flops, and j. the aforesaid ring counter output terminals being the points intermediate the Q output terminals and data input terminals of successive flip-flops.

2. A device for implantation in a body to affect a physiological function, comprising:

a. means for producing electrical signals for affecting said function, b. control means for altering at least one operating characteristic of said signal producing means, c. at least one and another magnetically operable switch means interconnected with said control means, each of said switch means being operable between conductive and nonconductive states under the influence of a magnetic field, said control means responding to said switch means being in predetermined states by altering said characteristic, d. said switch means being arranged for a magnetic field of predetermined configuration to change at least one of said switch means to its said predetermined state while said at least another switch remains in a said predetermined state, e. said at least one switch means being normally open and nonconductive and said at least another switch means being normally closed and conductive, said switch means being in their predetermined states when they are closed, said switch means being arranged near each other for a stray magnetic field which is capable of closing and normally open switch means to also open said normally closed switch means.

3. The device set forth in claim 2 wherein:

a. said normally closed switch means is susceptible to opening under the influence of a magnetic field that is weaker than that required to close said normally open switch means.

4. The device set forth in claim 2 wherein:

a. said one and another switch means are normally open and nonconductive and normally closed and conductive, respectively, b. third normally conductive magnetically operable switch means connected in a circuit with said one and another switch means, said another and said third switch means being arranged in spaced relationship relative to each other and to said one switch means for said magnetic field of predetermined configuration to intercept and close said one switch means and for a stray magnetic field which is intercepted by at least one of said another and said third switch means to open at least one switch means to prevent response of said control means even though said stray magnetic may also close said one switch means.

5. An implantable cardiac pacer comprising:

a. pulse generator means for applying stimulus pulses to the heart, said pulse generator means having at least one operating characteristic that is subject to alteration, b. means for altering said characteristic in response to control signals, c. circuit means including magnetically operable switch means for supplying control signals to said means for altering said characteristic, at least one of said switch means being normally open and closeable under the influence of a magnetic field to supply a control signal and at least another of said switch means being normally closed and operable under the influence of a magnetic field, d. said switch means being arranged for a magnetic field which couples simultaneously with both of said switch means to open said normally closed switch means and close said normally open switch means to thereby prevent supplying a control signal and for a magnetic field which couples with at least said one switch means without effectively coupling with said other switch means to close said one switch means and thereby permit supplying a control signal to said means for altering a characteristic.

6. An implantable cardiac pacer comprising:

a. pulse generator means for applying stimulus pulses to a heart, said pulse generator means having at least one operating characteristic that is subject to variation, b. means responsive to control signals by varying said characteristic, c. plural switch means operable between conductive and nonconductive states for controlling said control signal responsive means, at least one of said switch means being normally in one state and spaced from the other by a predetermined distance, said one switch means and the other being required to change their states in coincidence for controlling said control signal responsive means.

7. The device set forth in claim 6 wherein:

a. said at least one switch means is magnetically operable and in a normally nonconductive state and said other switch means is magnetically operable and in a normally conductive state, all of said switch means being serially connected, said one switch means being operable to change states by spaced apart simultaneously existing magnetic fields that couple only with said one switch.

8. An implantable cardiac pacer comprising:
   a. pulse generator means for applying stimulus pulses to a heart, said pulse generator means having at least one operating characteristic that is subject to variation,
   b. means responsive to control signals by varying said characteristic,
   c. switch means in a circuit for supplying control signals to said control signal responsive means,
   d. said switch means comprising magnetically operable switches including a first normally open switch, a normally closed switch and a second normally open switch,
   e. said switch means being arranged for a magnetic field which couples with one or both of said normally open switches and simultaneously with said normally closed switches to at least open said normally closed switch to prevent establishing said circuit for supplying a control signal and arranged for a magnetic field to couple with both of said normally open switches to enable supplying a control signal.

9. A portable hand held device for controlling the states of magnetically operable switch means in an implantable cardiac pacer to change an operating characteristic thereof wherein certain of said switch means are spaced apart from each other and normally in one state and another of said switch means is normally in another state and all of said switch means are required to be in the same state simultaneously to cause a change in said characteristic, said device comprising:
   a. magnet means for producing substantially isolated magnetic fields corresponding in number with said switch means which are normally in said one state and with said magnet means spaced apart a predetermined distance from each other for magnetically coupling respectively with said spaced apart switch means to change their states while remaining substantially magnetically uncoupled from said other switch means to permit its state to remain unchanged,
   b. said magnet means being arranged with similar polarity poles of each of them adjacent each other and opposite polarity poles of each of them remote from said similar polarity poles and from each other, to provide a field free region between said adjacent poles, and
   c. resin encapsulating said magnet means and maintaining said magnet means at said predetermined distance, said resin and magnet means comprising a unitary device that must be placed in a substantially singular position proximate to said pacer to cause said switch means to be in said same state simultaneously.

10. A device for controlling the states of magnetically operable switch means in an implantable cardiac pacer to change an operating characteristic thereof wherein certain of said switch means are spaced apart from each other and normally in one state and another of said switch means is normally in another state and all of said switch means are required to be in the same state simultaneously to cause a change in said characteristic, said device comprising:
   a. means for producing substantially isolated magnetic fields corresponding in number with said switch means which are normally in said one state and spaced apart from each other by a sufficient amount for coupling respectively with said spaced apart switch means to change their states while remaining substantially magnetically uncoupled from said other switch means to permit its state to remain unchanged,
   b. said magnetic field producing means being arranged with similar polarity poles of each of them adjacent each other and opposite polarity poles of each of them remote from said similar polarity poles and from each other, to provide a field free region between said adjacent poles,
   c. means for supporting said magnetic field producing means, and
   d. said magnetic field producing means comprising first and second permanent magnets and magnetically permeable members magnetically coupled with said similar polarity poles, respectively, and each terminating in a region intermediate said similar and opposite poles, respectively, to effect a field free region between them.

11. A hand held device for operating magnetically operable switch means in an implantable cardiac pacer to change an operating characteristic thereof which switch means comprise a normally open first magnetically operable switch, a second normally closed magnetically operable switch and a third normally open magnetically operable switch, said switches being serially connected in the stated order, said device comprising:
   a. at least a pair of magnet means arranged with poles of the same polarity adjacent each other and poles of opposite polarity spaced remotely from each other and remotely from said poles of same polarity to produce individual magnetic fields extending from the corresponding adjacent poles of each magnet to their respective other polarity poles with no substantial magnetic field between said magnets, said fields being spaced apart sufficiently to couple simultaneously only with said first and third normally open switches in said pacer to close the same without operating said normally closed switch in said pacer, and
   b. resin encapsulating said magnet means, said resin and magnet means comprising a unitary device that must be placed in a substantially singular position proximate to said pacer to close said normally open switches without opening said normally closed switch.

* * * * *